United States Patent [19]

Vasington et al.

[11] Patent Number: 4,778,749

[45] Date of Patent: Oct. 18, 1988

[54] TISSUE CULTURE AND PRODUCTION IN PERMEABLE GELS

[75] Inventors: Paul J. Vasington, Norwood, Mass.; Maurice M. Lynch, Warwick, R.I.; Maureen E. Frye, Mansfield, Mass.

[73] Assignee: Karyon Technology, Inc., Norwood, Mass.

[21] Appl. No.: 816,534

[22] Filed: Jun. 1, 1984

[51] Int. Cl.$^4$ .................. A01N 1/02; C12P 21/00; C12N 5/00

[52] U.S. Cl. .................................. 435/2; 435/68; 435/240.22; 935/106

[58] Field of Search ............... 435/68, 178, 182, 240, 435/241, 286, 2, 948, 172.2; 935/106, 108

[56] References Cited

U.S. PATENT DOCUMENTS

| | | |
|---|---|---|
| 3,733,205 | 5/1973 | Shovers et al. |
| 3,793,445 | 2/1974 | Updike et al. ........................ 424/12 |
| 4,061,466 | 12/1977 | Sjoholm et al. ..................... 436/535 |
| 4,257,884 | 3/1981 | Lim .................................... 435/182 |
| 4,311,690 | 1/1982 | Buehler et al. ........................ 424/1 |
| 4,322,311 | 3/1982 | Lim et al. ............................. 424/85 |
| 4,324,683 | 4/1982 | Lim et al. ............................ 424/101 |
| 4,334,027 | 6/1982 | Klein et al. ......................... 435/178 |
| 4,352,883 | 10/1982 | Lim .................................... 435/178 |
| 4,353,888 | 10/1982 | Sefton ................................... 435/2 |
| 4,386,158 | 5/1983 | Shimizu et al. ...................... 435/178 |
| 4,391,909 | 7/1983 | Lim .................................... 435/178 |
| 4,399,219 | 8/1983 | Weaver ................................ 435/34 |
| 4,401,755 | 8/1983 | Weaver ................................ 435/39 |
| 4,407,957 | 10/1983 | Lim .................................... 435/182 |
| 4,409,331 | 10/1983 | Lim .................................... 435/241 |
| 4,452,892 | 6/1984 | Rosevear ............................ 435/178 |

FOREIGN PATENT DOCUMENTS

| | | | |
|---|---|---|---|
| 0114756 | 8/1984 | European Pat. Off. ............ 435/182 |
| 0121400 | 10/1984 | European Pat. Off. ............ 435/182 |
| WO81/01098 | 8/1981 | PCT Int'l Appl. . |
| 2036032 | 11/1979 | United Kingdom . |

OTHER PUBLICATIONS

Messing, "Immobilized Microbes", Annual Reports on Fermentation Processes, vol. 4 (1980), pp. 105–121.
Abbott, "Immobilized Cells", Annual Reports on Fermentation Processes, vol. 2 (1978), pp. 91–123.
Kupchik et al., Exp. Cell Res. 147, pp. 454–460 (1980).
Advances in Applied Microbiology, vol. 28, P. Brodelius and K. Mosbach (1982).
Science, vol. 210, pp. 908–910, Franklin Lim and Anthony M. Sun, (Nov. 21, 1980).
Chibata et al., Academic Press, vol. 1, pp. 329–357 (1976).
Methods in Enzymology, vol. 44, K. Mosbach, ed., Academic Press, New York (1976), pp. 3–7.
FEBS Letters, 103, 93–97, (1979), P. Brodelius et al.

*Primary Examiner*—John E. Tarcza
*Attorney, Agent, or Firm*—Gregory D. Williams; David G. Conlin

[57] ABSTRACT

Methods are disclosed for entrapping, proliferating, and/or preserving biological material such as tissues and cells wherein the biological material is entrapped in a permeable gel-like material. The entrapped material is nurtured and proliferated in the gel-like microenvironment. Metabolic and/or other products are thereafter harvested from the entrapped material.

17 Claims, 1 Drawing Sheet

TISSUE CULTURE AND PRODUCTION IN PERMEABLE GELS

FIELD OF THE INVENTION

The present invention relates to a process for entrapment and growing cells and tissues in an artificial environment. More particularly, the present invention deals with methods and related products for entrapping living biological materials such as tissues and cells in a permeable gel-like material, nurturing and growing such cells within the gel-like minienvioronment while supplying needed nutrients and other materials through the permeable gel from a macroenvironment, and harvesting the metabolic and/or other products or byproducts. The present invention permits in vitro cell culture and growth to high cell densities, increased yields of biologically produced products and many other benefits.

BACKGROUND OF THE INVENTION

Over the years, there has been considerable interest in the encapsulation or immobilization of living cells, particularly those of microbial origin. See generally, K. Mosbach, Ed., *Methods in Enzymology*, Vol. 44, Academic Press, New York, 1976; B. J. Abbott, *Ann. Rpt. Ferm. Proc.*, 2:91 (1980); R. A. Messing, *Ann. Rpt. Ferm. Proc.*, 4:105 (1980); Shovers, et al. U.S. Pat. No. 3,733,205 (1973). Interest has been extended to the immobilization of plant cells in suspension. P. Brodelius et al., *FEBS Letters*, 103, 93–97 (1979).

More recently, efforts have been concentrated in processes for encapsulating tissue and individual cells, particularly mammalian cells, so that they remain viable and in a protected state within a membrane which is permeable to the plethora of nutrients and other materials required for normal metabolic functions.

One such technique is described in U.S. Pat. No. 4,391,909, wherein tissue cells such as Islet of Langerhans cells are encapsulated within a spherical semipermeable membrane comprising a polysaccharide having acidic groups which have been cross-linked for permanance of the protective membrane. The semipermeable membrane has a selected limit of permeability of no greater than about 200,000 daltons, so that serum proteins and other high molecular weight materials necessary for growth can be sealed with the living cells within the semipermeable membrane, while other, smaller molecular weight metabolites and nutrients can traverse the membrane wall and be interchanged with the outside media. The process therein disclosed comprises suspending the tissue to be encapsulated (and the high molecular weight nutrients) in a physiologically compatible medium containing a water soluble substance that can be made insoluble in water (i.e., gelled), to provide a temporary protective environment for the tissue. The medium containing the tissue is next formed into droplets by forcing the tissue-medium-nutrient suspension through a teflon coated hypodermic syringe, the tip of which is subjected to laminar air flow which acts as an air knife. See also U.S. Pat. No. 4,352,883, wherein the spheres are formed by forcing the materials trough a capillary tube into the center of a vortex created by rapidly stirring a solution of $Ca^{+2}$ cation. The medium, e.g. a polysaccharide gel, is temporarily gelled in a generally spherical shape by contact with the calcium solution. Thereafter, these "temporary capsules," are provided with permanant polymeric semi-permeable membranes at their outer layer, formed by permanently cross-linking or polymerizing the capsules with polymers containing reactive groups which can react with specific constituents of the polysaccharide.

Thus until the present invention, entrapment in aqueous gels alone was considered as only a "temporary" vehicle, around which a permanent membrane could be formed. Generally, following the formation of the permanent membrane, the "temporary" gel was dissolved, so that any cell growth achieved thereafter was not in the presence of the gelled substance.

Such complex prior art processes are not without limitations. For instance, with mammalian cells, although it has been possible to encapsulate viably and metabolically active cells within hardened semipermeable membranes, promotion of growth therein has not been satisfactory. Moreover, cell densities thus far achievable within such membranes has been less than about $10^6$ cells per milliliter of culture media. Both of these limitations affect the amount and recovery of useful and desirable cell products produced by the entrapped material. The ability to grow cells to higher cell densities within a protected environment (capsule) would provide a means for achieving greater output of desirable cell products.

A further disadvantage of prior art methods of entrapping animal cells is the inability to maintain cell viability at desirable higher cell densities. FEBS P. Brodelius et al., *FEBS Letters*, supra, where entrapment of mammalian cllls resulted in a lack of proliferation of cells and a cell viability of about 10–30% after incubation in tissue culture for one (1) week.

SUMMARY OF THE INVENTION

In one aspect, the present invention provides a process for proliferating cells within an artificial gel-like environment. The methods and products involved permit the growth of mammalian cells in in vitro tisue culture media to greater than normal (unentrapped) cell densities, the maintenance of high cell viability in such material, and the collection of by-products produced as a result of entrapped cell metabolism.

The basic approach involves suspending the cells in a polysaccharide gum, preferably an alkali metal alginate such as sodium alginate and thereafter forming the suspension into droplets. The droplets thus formed are gelled in a calcium cloride solution, washed and grown in culture media to proliferate cells entrapped therein.

More specifically, the present invention provides a process for proliferating viable mammalian and hybridoma cells within a semipermeable gel-like membrane. As noted above, it has previously been difficult to maintain viable mammalian cells in an artificial environment at levels greater than 10-30% viability. It has also been extremely difficult to grow mammalian cells in artificial environments, i.e. capsules, particularly at cell densities where commercial quantities of cell products are produced. The present invention overcomes such obstacles in that it allows entrapment of viable cells, such as mammalian and hybridoma cells, at viabilities exceeding 50% and at cell densities where desirable cell products can be economically harvested for commercial use.

In another aspect of the present invention, there is provided a process for producing substances which are produced by viable cells which comprises the above-described entrapment technique.

DETAILED DESCRIPTION OF THE INVENTION

Figure 1:
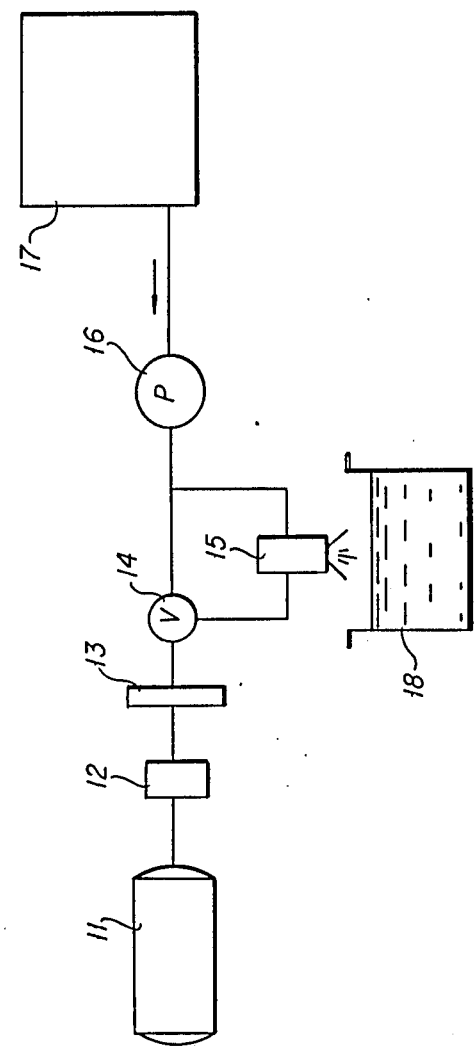
FIG. 1 shows a schematic depiction of one embodiment of various apparatus which are useful in connection with the present invention.

It has now been discovered that mammalian and other living cells can be entrapped in hydrophilic gels by a method and using apparatus which is much simpler than those previously used, that such entraped cells can be grown to large cell densities and maintained for substantial periods of time, without the need for an additional selectively permeable membrane surrounding the entrapped cells; that such entrapped cells can be used to produce high levels of metabolic or other cellular products, such as monoclonal antibodies; and that, after a suitable period wherein the production of the desired material(s) is maximized, the used but viable cells can be recovered for reuse by resolubilizing the hydrophilic gel to release the entrapped cells, followed by re-entrapment using the same procedure, as described above.

The present invention is particularly well suited for the production of monoclonal antibodies using hybridomas entrapped in a hydrophilic gel. However, other cell types, particularly mammalian cell types can also be used to advantage to produce other products in accordance with the present invention. Other types of cells which can be used to produce desired products include various types of T-cells, e.g. helper T-cells, suppressor T-cells, B-cells, mast and stem cels, hormone-producing cells from the pituitary or other glands or tissues in the body; and other tissue which produces or can be modified to produce the product of interest.

The hydrophilic gel used for entrapment is preferably an alginate, which is a natural hydrocolloid derived from seaweed, although other hydrophilic materials such as agarose, agar, carrageinan, xanthan gum, polyacrylamides, poly HEMA, and others known in the art can be used to advantage in particular environments.

Preferably, the microenvironments which contain the cells, the hydrophilic gelling agent and various nutrients and accessory materials, are formed into discrete particles, preferably generally spherically shaped particles. Preferably, the gelled particles are mobile and thus can be arranged for convenient culturing, treatment and product extraction. Thus, for example, the entrapment beads can be arranged, nurtured, or extracted in packed beds, fluidized beds, in stirred containers, in continiuous reactors or treatment units, which themselves are known in the art, e.g. similar to those used for treating ion exchange resins, etc. The conditions of treatment, including temperature, pressure, solvent, and physical treatment should be chosen so that the entrapment beads retain their particulate nature.

The condition of treatment of the entrapment beads should also be chosen to maintain viability and growth of the cells contained within the beads. Thus, the beads should not be exposed to extremes of temperature, pH, or to toxic chemicals, for amounts of time which would cause loss of viability of the desired cells. Preferred temperature ranges are from about 0° C. to about 50° C., preferably between about 15° C. and about 40° C. For many cell systems, growth is optimized at temperatures around 37° C. The preferred range of pH at which the entrapment gels are maintained is between about 5 and 9, preferably between about 6 and 8. Various steps in treatment of the beads may require different pH's, and pH values outside of the broad ranges can often be tolerated by the cells for limited periods of time without deleterious effect.

Cell viability and growth normally require access to a source of oxygen for respiration, as well as various nutrients, vitamins, amino acids, salts, and other components, known per se for various cell types. Normally some of these nutrients and other factors will be entrapped within the bed along with the cells, so that continuous growth for some periods of time can be maintained without further additions of such factors. However, culture of such cells for production of proteins or other metabolites or products require considerable time, and such production is normally optimized by providing the cells with ready acess to the required nutrients and other ingredients. Thus, the entrapment beads are preferably suspended in or otherwise contacted with a fluid containing oxygen, nutrients, vitamins, minerals, etc., wich can diffuse through the hydrophilic gel to the cells and thus maintain viability and growth.

As shown in FIG. 1, one apparatus utilized in entrapping the cells in accordance with the present invention involve a controlled source of sterile air, means for admixing the cells to be grown with the hydrophilic gel-forming material while such material is in liquid form, means for feeding the sterile air and admixed cells/hydrogel to a standard gas/liquid atomizing spray head, and a reservoir of material which receives and gels the droplets formed by the spray head.

Thus, as shown schematically in FIG. 1, the apparatus used in the preferred embodiment comprises a compressor or other source of compressed air 11, an air flow meter 12, an air filter 13, which has an effective pore size of 0.22 $\mu$m (micron) or less, so as to sterilize the air used. The sterilized air then proceeds through a control valve 14, to a conventional two phase spray head 15, where it mixes with the liquid cell/hydrogel mixture.

The liquid cell/hydrogel mixture is preferably formed in a tank 17, and is fed to spray head 15 through a pump 16, which is preferably a controlled constant volume, peristaltic pump as in known in the art.

In the spray head 15, the liquid is forced out a small diameter (0.006–0.016 mil) cylindrical top, which is surrounded by an annular air passageway. The air contacting the droplets formed at the end of the top frees the droplets from the tips. The droplets are then propelled out into the atmosphere in the form of fine spherical droplets. The droplets then contact the liquid in container 18, which contains a divalent cation gelling agent, which gels the liquid droplets, such as a calcium chloride solution, where the hydrogel used is sodium alginate. Other divalent cation gelling agents include the other alkaline earth metals (except magnesium), other divalent metals, and divalent organic cations, such as ethylene dismine. Preferably, the tank 17 and container 18 are both stirred during the process at slow speeed, in order to keep the solids from settling out and maintain constant concentration.

As noted above, previous attempts to grow mammalian cells in hydrogels, particularly without a porous outer semipermeable membrane, have met with little or no growth rate and poor viability. It has now been found that, by controlling particle size and the type of hydrogel used, mammalian cells can be entrapped or encapsulated and grown to high densities, with substantially improved viability of cells.

One important factor is the type of hydrogel to be used. Highly preferred are clarified long-column sodium alginates, such as Kelco-Gel HV and Kelco-Gel LV, sold by Kelco Company (San Diego). These are sodium alginates which are fibrous in nature, are supplied at a neutral pH, (typically about 7.2) and contain approximately 80% carbohydrates, 9.4% sodium, 0.2% calcium. 0.01% magnesium, and 0.1% potassium. Kelco-Gel HV has the higher molecular weight, having a Brookfield viscosity of about 400 (1% water solution) to about 3500/2% water solution) centipoise wherein Kelco Gel LV has a viscosity of about 50 (1% solution) to about 250 (2% solution). Of these products, the Kelco Gel HV is highly preferred.

Preferably, the hydrogel is further clarified and sterilized before use by passage through a sterile filter having a pore size of 0.2/2 microns or smaller. Preferably, a Pall filter is used in the clarification/sterilizaton step.

Preferably, the flow rates of gas and liquid are adjusted so that the size of the particles or droplets formed ranges from about 0.4 to about 2 mm in diameter. The flow rates depend to some extent on the viscosity of the liquid hydrogel, which in turn depends on the type and concentration of the hydrogel used. The provision of from about 0.4 to 2 millimeter particles, preferably about 0.6–1.5 millimeter particles, permits sufficient diffusion of nutrients and accessory growth factors into the particles to provide for cell growth. Substantially larger gel/cell particles tend to decrease the growth and viability rates of the cells.

The concentration of hydrogel in the mixture should range from about 0.5 to about 1.4%, preferably about 0.6 to 1.2%, most preferably about 0.7–0.9%. This is considerably below percentages previously used, and is believed to result in higher porosity of the gel beads to nutrients and other factors. Attempts at making beads below a 0.5 mm in diameter have met with difficulty, even with the fairly viscose Kelco Gel HV, and especially with Kelco Gel LV.

A key feature is to achieve cell containing hydrogel beads with sufficient porosity and an appropriate size for diffusion of the nutrients to the cells in the inner reaches of the beads. While the Kelco Company products mentioned have been utilized in overcoming the problems of the prior art and growing mammalian cels in an encapsulated environment, many simlar or alternative hydrogels exist in the art and are commercially available. It having been shown that improved growth and viability rates can be obtained from such materials without use of the overcoating method of Lim, the skilled in the art can adjust the process to other simlar materials.

It is important that no semipermeable layer be formed on the outside of the hydrogel cell beads, either by cross linking of the hydrogel or by coating with a further polymer, for a number of reasons. Such coatings interfere with the free diffusion into and out of the hydrogel beads. Moreover, the hydrogel beads of the present invention permit recycling and reuse of the cells contained therein, simply by dissolution of the hydrogel, which leaves the cells intact, and free from any non-cellular material. This could not be done if the cells are enveloped in an insoluble polymer coating.

The spray head or nozzle utilized in connection with this invention need not be the modified hypodermic syringes so intricably modified in previous products. Rather, standard off the shelf biphasic spray heads can be utilized to advantage in making the desired beads. Suitable spray heads include those sold by Spraying Systems, Inc., such as products sold under the designations ⅛ and JACN, ⅛ JACN ⅛ JBg. Other suitable nozzles are available in the art. Preferably, the nozzles used in this invention are beveled at the outside of this tip to form a conical tip, the sides are sloped at 15° or 30° to the longitudinal axis of the top, to direct the air flow at more of an angle to the droplets formed. Such an angle can be simply ground into the liquid tip orifice. Preferred inner diameters for the liquid spray tip include 0.006", 0.010" and 0.016", with the smaller sizes preferred, to produce smaller droplets.

A typical example of gel entrapment follows: Cells at a concentration $10^6$ cells/ml are suspended in a solution of 1.5% (w/v) solution of sodium alginate in normal saline. This suspension is placed in a suitably sized vessel. Where the production run is to take considerable time, so that the cells will be out of contact with media for considerable time, nutrients and other materials can be added to the alginate suspension and/or to the multivalent gelling agent solution. A typical addition would include 50 mm of glucose, 1X of essential amino acids, 1X of nonessential amino acids, 1X of vitamins and/or any other needed growth factors. A tube from this vessel is connected to the liquid inlet of the spray head apparatus. Another tube containing compressed air is connected to the air inlet of the spray head apparatus. The liquid is pumped through the spray head at the same time compressed air is blown through the spray head. The resultant sodium alginate cell suspension droplets are blown into the gelling solution of calcium chloride. The contact with calcium ions causes the immediate formation of a gel (calcium alginate) which entraps the cells contained within the gel droplet. Upon complete formation of all droplets, the droplets are removed from the calcium chloride solution, washed several times in normal saline solution and placed in the appropriate tissue culture medium. Entrapped cells have been shown to divide and metabolize for over three weeks in these permanent calcium alginate gels. Cells are capable of attaining higher cell densities than if grown in normal tissue culture. The cell viabilities at these higher densities has been shown to remain high (°50%). By-products from cell metabolism have been collected from these gel-entrapped cell cultures.

For example, hybridoma cells (i.e. cells produced as a result of fusing spleen cells or antibody producing cells with a myeloma cell line either intra-or interspecies) may be entrapped in a calcium alginate gel-like material. These hybridoma cells may be obtained commercially, e.g. from the American Type Culture Collection, Rockville, Md., or may be prepared by any individual skilled in the art of tissue culture, immunology and hybridoma development. See ATCC Catalog, *Cell Lines, Viruses, Antisera,* 192 et seq (ATCC 1983); Kohler and Milstein, *Nature* 256:495 (1975), the disclosure of which is incorporated herein by reference. Each individual hybridoma cell line may have its own unique set of growth requirements, i.e. type of tissue culture media and type and amount of nutrients required, as is recognized by individuals skilled in the art.

Under normal in vitro tissue culture conditions, most hybridoma cell lines grow to densities of $10^5$–$2 \times 10^6$ cells/ml of tissue culture media. These cells typically produce monoclonal antibodies in vitro at levels of 1–10 $\mu$g/ml/day of culture media dependent on the cell line.

Growth of cells to higher cell densities, as attained in the present invention, effectively increases the yield of monoclonal antibody/ml of culture media resulting in significant space and cost advantages. Entrapment of hybridoma cells in calcium alginate provides the means by which cell densities can be increased above $2 \times 10^6$ cell/ml and for production of monoclonal antibody at levels above the normal 1-10 µg/ml. On procedure for achieving such production is described as follows:

Using aseptic procedures, cells from a particular hybridoma cell line are separated from their culture fluid by low speed centrifugtion ($500 \times G$) in sterile conical test tubes. The supernatant is removed and the cells are suspended to a concentration of $1 \times 10^5$-$2 \times 10^6$ cells/ml in a sodium alginate solution (e.g., Kelco Gel HV) at a concentration of 0.5-2.0%, preferably 0.6-1.5%, preferably in normal saline.

All work is carried out using aseptic techniques in a laminar flow hood. Air pressure is adjusted to 0-10 SCFH (standard cubic feet per hour) using the air flow meter 12 (e.g. Dwyer Flow Mates #SS-2MHL-25). All equipment and tubing which the alginate cell suspension passes through has been sterilized. A 0.22 µm in-line air filter (e.g. Millipore Millex-GS) sterilizes the air prior to its passage through the spray head assembly.

A sterile glass beaker containing an excess volume of sterile calcium chloride (0.65-1.5% w/v) is placed on a magnetic stirring plate below the spray head assembly such that the bottom of the spray head assembly is 5-10 inches above the surface of the calcium chloride solution. A sterile magnetic stir bar is placed in the calcium chloride. The magnetic stir plate is set at low speed.

The outflow tube of the peristaltic pump (e.g. Rainin "Rabbit") is connected to the liquid inlet of the spray head assembly, (e.g. Spraying Systems ⅛ JACN). The inflow tube of the peristaltic pump is inserted into the sodium alginate/cell suspension. The air tube is connected to the spray assembly and the air flow meter adjusted to 0-10 SCFH. The pump is turned on and adjusted so that the flow rate is 0-10 ml sodium alginate-cells/min. Droplets formed using this procedure fall into the solution of calcium chloride where sodium ions are replaced by the higher affinity calcium ions resulting in increased cross-linking of the alginate and formation of a stable calcium alginate gel containing entrapped hybridoma cells.

After the last gel droplet is formed, the calcium alginate beads are allowed to settle out in the calcium chloride. The supernatant is aspirated and sterile saline is added to bring the volume to its original level. This step is repeated two additional times. Following the last wash, the supernatant is aspirated and the calcium alginate beads are placed in media suitable for that particular hybridoma cell line so that the concentration of alginate beads is between 10-20% for a stirred culture vessel. Higher concentrations of alginate beads (up to 90%) may be achievable using a fluidized bed, continuous feed culture system.

The gel-entrapped hybridoma cells are incubated at 37° C. and allowed to grow to their optimum cell density. The culture supernatant is removed and replaced with an equal volume of fresh supplemented culture growth medium as needed. Continuous feed systems may automatically replenish the media on a continuous basis. The entrapped hybridoma cells produce and secrete monoclonal antibody into the surrounding culture media. At optimum cell densities ($10^7$-$10^8$ cells/ml of calcium alginate), the hybridoma cells will produce antibody at the rate of 10-100 µg/ml/day or greater. The supernatant containing the monoclonal antibody may then be concentrated by conventional techniques to allow further purification of monoclonal antibody using techniques known by individuals skilled in the art.

Additionally, the calcium alginate entrapped cells can be harvested and re-used by dilution of the calcium ions with chelating agents such as solutions of sodium ctrate (10% w/v) ethylene diamine tetraacetic acid, (EDTA) sodium salt of etylene glycol-bis (An aminoethyl ether) $NN^1$-$N^1$-tetra acetic acid (EDGA) which sequester or chelate the calcium ions causing reformation of the liquid sodium alginate. The hybridoma cells can then be harvested from the sodium alginate.

From the forgoing it will be apparent that the process for proliferating cells in an entrapped environment and harvesting cell products therefrom can be practiced for a wide variety of cells and cell products without departing from the scope and spirit of the invention. The following examples should accordingly be construed in all respects as illustrative and not in a limiting sense.

EXAMPLE I

Human red blood cells were added to a 1.2% sodium alginate solution to give a final concentration of $2.5 \times 10^5$ cells per ml in 1.0% sodium alginate. The solution was then conveyed by a Rainin Rabbit peristaltic pump to a sprayer assembly. Compressed air was supplied at 20 PSI through air tubing to a Dwyer airflow regulator and thereafter through 0.22 µm filter (Millipore Millex-GS) and then to the sprayer assembly. Droplets were formed at the sprayer assembly which contained human red blood cells. The droplets were deposited in a sterile beaker containing a 1.33% w/v calcium chloride solution from a height of 3 cm. The beaker was stirred with a magnetic mixer at low speed and the droplets were allowed to gel. The gelled droplets were allowed to remain in the gelling solution for up to 30 minutes. The gelling solution was therefter washed and the gelled droplets were resuspended in medium containing various concentrations of pyruvate and/or adenine in HEPES buffer. Red blood cells have been preserved in this fashion without hemolysis for 60 days.

This example shows methods by which red blood cells can be preserved for weeks. There is a substantial need for standards with which to standardize instruments and size measurement devices such as Coulter counters and other instruments. The preservation method of the present invention can be used to stabilize blood platelets or other materials for transportation and storage of sensitive cells like blood platelets. Blood platelets normally degrade after relatively short periods and form Meta hemaglobin, the dark brown decomposition product. Preservation agents such as formaldehyde can effect the size and shape of the platelets, and in any event are inadequate to preserve such cells for long periods or many uses. Platelets entrapped and stirred in accordance with the present invention remain viable, healthy and uniform in shape, thus making them suitable for use and reuse over long periods of time.

EXAMPLE II

A hybridoma cell line was obtained from the American Type Culture Collection (ATCC). The cell line, designated as ATCC No. CRL-9017 (H25 B10) produces antibodies to Hepatitis B surface antigen (Ig $G_1$ Isotype). Its culture medium was a Dulbecco's Modified Eagles medium, 4.55 g/l glucose; and Fetal Calf serum, 10% or less.

The gelling solution was prepared to have of final makeup of 1.3% CaCl$_2$.2H$_2$O, 0.5% glucose in 3 mM HEPES pH 7.7. A first wash solution contained a 1:1 mixture of the gelling solution with 0.9% saline. The second wash solution contained a 1:1 mixture of the first wash solution with 0.9 saline. The sodium alginate-cell suspension was a mixture of 1.2% sodium alginate with one part of cell suspension to make a final concentration of $2.0\times10^6$ cells per ml of sodium alginate.

The hybridoma cells from ATCC No. CRL-8017 (H25 B10) were encapsulated as follows:

The sodium alginate-hybridoma suspension was conveyed through the silastic 1/16" I.D. tubing by the peristaltic pump with was set at 350 to give a rate of approximately 2.5 ml/min to the sprayer. Air pressure was supplied to the sprayer assembly at 10–20 PSI. It was independently conveyed to the sprayer assembly by the 1/16" I.D. Slastic tubing through the Dwyer Gauge at SCFH Setting 3. From the air flow gauge the air passed through the Millex air filter to the spray assembly. (NB. all fittings from the air filter to the spray assembly were autoclaved at 15 PSI for 15 minutes). A beaker containing the gelling solution was placed directly below the spray assembly with a distance of about 3–4 cm between the spray orifice and the surface of the solution. A magnetic stir bar was placed in the beaker and the gelling solution agitated at low speed. Droplets of the sodium alginate-hybridoma suspension formed at the oriface of the spray assembly and dropped into the gelling solution where they were allowed to remain for about 3 minutes after the spraying operation. The gelling solution was then aspirated and the capsules were resuspended in the first wash solution and allowed to settle. After 5 minutes the solution was aspirated in the same fashion as before. The capsules were resuspended in the second wash solution and again aspirated. Upon completion of the washing evolution, the capsules were placed in the above described medium at a concentration of 20% capsules.

The gel entrapped hybridoma cells were incubated at 37° C. and allowed to grow to optimum densities in approximately 11 days. At 3 day intervals or when phenol red indicator changes to yellow, the vessel fluids were evacuated and fresh nutrient media added. Fetal calf serum supplement was reduced from 10% to 0% at the third change of medium. The sequestered cluster of hybridoma cells excreted monoclonal antibodies (IgG) into the medium. The medium containing these antibodies ws removed for harvest. The fluids were concentrated with 50% ammonium sulfate and further purfied through affinity columns. The gel entrapped cells were placed in a sodium citrate solution which converted the calcium alginate gel to sodium alginate liquid, releasing the hybridoma cells which, were gel entrapped in a repeating cycle or production.

EXAMPLE III

A second hybridoma cell line was obtained from the ATCC with ATTC No. CRL-1644 (SJK-287-38). This cell line produces antibodies reactive with DNA polymerase aplha. Its culture medium was a Dulbecco's Modified Eagles medium (10 mM) 100 ml; glutamine 100×, 1 ml; non-essential amino acids, 100×, 1 ml; NCTC109, 10 ml; Fetal bovine serum, 12 ml; and 1 ml of the solution prepared as follows:

(a) 1320 mg oxaloacetic acid (b) 80 mg crystalline insulin (20 units/ml; 25 units 1 mg)

(c) stir (a) and (b) at 37° C.

(d) add 550 mg sodium pyruvate (50 mM)

(e) bring to 100 ml with distilled water and continue stirring until dissolved (Filter and Sterilize).

These hybridomas were entrapped and propagated in gel beads as described in Example II.

What is claimed is:

1. A process for proliferating viable mammalian cells, said process comprising:
   (a) suspending said cells in an alkali metal alginate solution wherein said alkali metal alginate is selected from the group consisting of low viscosity gels having a viscosity of about 50 centipoises in a 1% solution to about 250 centipoises in a 2% solution and high viscosity gels having a viscosity of about 400 centipoises in a 1% solution to about 3500 centipoises in a 2% solution at 25° C.;
   (b) forming the suspension into droplets;
   (c) gelling said droplets to form shape-retaining structures about said cells;
   (d) placing said cell containing structures in a growth medium which promotes proliferation of said cells; and
   (e) growing said cells to concentrations substantially greater than obtainable by conventional cells culture technique within said structures to proliferate cells entraped therein without the additional formation of a membrane.

2. The process of claim 1, wherein said alkali metal alginate solution is from about 0.6–2.0% w/v dissolved in physiological saline.

3. The process of claim 2, wherein said alkali metal alginate is sodium alginate.

4. The process of claim 1, wherein said droplets are gelled by contacting said droplets with multivalent cation gelling agent.

5. The process of claim 4, wherein said multivalent cation gelling agent is a solution containing about 0.6–1.5% w/v of calcium chloride.

6. The process of claim 1, wherein said gelled droplets range in size from about 0.5 mm to about 2 mm in diameter.

7. The process of claim 1, wherein said mammalian cells proliferate to cell densities greater than about $5\times10^6$ cells/ml.

8. The process of claim 1, wherein said cells are hybridoma cells.

9. The process of claim 8, wherein said hybridoma cells proliferate to cell densities greater than about $5\times10^6$ cells/ml.

10. The process of claim 1, wherein said cells having been genetically modified.

11. A process for producing a substance which is produced by viable mammalian cells, said process comprising:
    (a) suspending said cells in an alkali metal alginate solution wherein said alkali metal alginate is selected from the group consisting of low viscosity gels having a viscosity of about 50 centipoises in a 1% solution to about 250 centipoises in a 2% solution and high viscosity gels having a viscosity of about 400 centipoises in a 1% solution to about 3500 centipoises in a 2% solution at 25° C.
    (b) forming the suspension into droplets;
    (c) gelling said droplets to form shape-retaining structures about said cells;

(d) placing said encapsulated cells in a growth medium which promotes proliferation of said cells and proliferating said cells therein to concentrations substantially greater than obtainable by convention cell culture technique without the additional formation of a membrane;

(e) allowing said cells to undergo metabolism invirto to produce said substance; and (f) harvesting said substance.

12. The method of claim 11, wherein said cells comprise hybridoma cells.

13. The method of claim 11, wherein said alkali metal alginate is sodium alginate and said droplets are gelled by contacting said droplets with a calcium chloride solution.

14. The method of claim 11, wherein said substance is harvested from said encapsulated cells.

15. The method of claim 11, wherein said substance diffuses into and is harested from said growth medium.

16. The process of claim 11, wherein said cells have been genetically modified.

17. The process of claim 11, wherein said gelled droplets range in size from about 0.6 mm to about 2 mm in diameter.

* * * * *